United States Patent
Goltra

[11] Patent Number: 5,823,949
[45] Date of Patent: Oct. 20, 1998

[54] INTELLIGENT PROMPTING

[76] Inventor: Peter S. Goltra, 22717 Goltra La., Middleburg, Va. 22117

[21] Appl. No.: 907,920

[22] Filed: Aug. 11, 1997

Related U.S. Application Data

[63] Continuation of Ser. No. 609,689, Mar. 1, 1996, abandoned.

[51] Int. Cl.⁶ ........................................ A61B 5/00
[52] U.S. Cl. ........................... 600/300; 128/924; 395/924
[58] Field of Search ............................. 600/300; 128/920, 128/923, 924; 364/274, 274.2, 274.3; 395/10, 50, 924

[56] References Cited

U.S. PATENT DOCUMENTS

| | | | |
|---|---|---|---|
| 4,839,822 | 6/1989 | Dormond et al. | 364/413.02 |
| 5,089,978 | 2/1992 | Lipner et al. | 364/551.01 |
| 5,262,943 | 11/1993 | Thibado et al. . | |
| 5,265,010 | 11/1993 | Evans-Paganelli et al. . | |
| 5,387,164 | 2/1995 | Brown, Jr. | 364/413.02 |
| 5,453,009 | 9/1995 | Feldman . | |

*Primary Examiner*—Jennifer Bahr
*Assistant Examiner*—Bryan K. Yarnell
*Attorney, Agent, or Firm*—Burns, Doane, Swecker & Mathis, L.L.P.

[57] ABSTRACT

A method and apparatus for helping healthcare professionals create clinical protocols or assist in direct entry of medical finding into a chart by intelligently prompting a healthcare professional with medical findings associated with at least one medical finding which has already been entered in the protocol is disclosed. First of all, at least one medical finding for a patient is inputted into the system wherein each finding is assigned a point value for each diagnosis within a knowledge base. A total number of points for each diagnosis is then totalled for all of the findings which have been entered into the system. The possible diagnoses are then ranked in descending point total and a predetermined plurality of the highest ranked diagnoses are selected. Once the highest ranked diagnoses have been selected, the healthcare professional is prompted with additional findings associated with the selected diagnoses which have not yet been inputted into the clinical protocol.

15 Claims, 2 Drawing Sheets

INTELLIGENT PROMPTING

This application is a continuation of application Ser. No. 08/608,689, filed Mar. 1, 1996, now abandoned.

FIELD OF THE INVENTION

The present invention relates to methods and apparatus for prompting a list of medical findings into a medical chart and more particularly to an electronic medical system which helps healthcare professionals create medical protocols or assist with direct entry by prompting the healthcare professional with a list of additional medical findings associated with the medical findings already entered into the protocol.

BACKGROUND OF THE INVENTION

While many aspects of the operation and administration at hospitals and other healthcare facilities have been computerized over the past years, one of the most important aspects, the generation of patient charts, the updating of these charts, the review of the chart, and the generation of care plans by healthcare professionals such as doctors, nurses, therapists, and the like, is still performed largely by hand. As a result, while a patient chart of some type is normally generated shortly after a patient is admitted to the healthcare facility for a particular service, for example, an intensive care unit, cardiac surgery unit, or the like, the chart may not always be updated to reflect actual progress by the patient.

When a patient comes into a health care facility, the patient may have numerous related or unrelated problems that the healthcare provider will have to sort through when determining what is wrong with the patient and what treatments should be prescribed for the patient. The diagnostic step in the treatment of the patient can thus be a very difficult process and a very important step in treating a patient. Today, most healthcare professionals must rely on their memory and experience as well as written materials when making a diagnosis. Unfortunately, all of the needed materials may not be available during the examination of the patient and thus important questions may not be asked or tests performed which could help the healthcare professional in determining the correct diagnosis for the problems being experienced by the patient. Thus, it would be advantageous to allow healthcare professionals to create medical protocols which prompt the healthcare professional with lists of questions that should be asked, symptoms to look for, and tests that should be run, during the examination process.

Even after a diagnosis has been made and a care plan for management of the patient has been devised, the patient chart may not be referred to when the healthcare professional is preparing progress notes on the patient. Thus, there is no check to assure that the original treatments have in fact been followed, or that proposed resolution dates in the chart have been met or updated. When changes in the chart are made as a result of changes in the status of a patient, such changes are frequently not entered in the original chart. Thus, good archival records are not generally maintained for changes in treatment. The professional notes for a particular patient frequently do not include an updated version of the patient's chart. Further, even though a form may be available for progress notes, the form does not take into account the unique problems of the individual patient, and does not give the healthcare professional a checklist of items to be investigated for such problems or suggested interventions or resolution dates for the particular patient problem. When changes are made or expected outcomes are not achieved, the reasons for such occurrences are seldom provided, making any further review far more difficult. Again, a good archival record of what has been done for the particular patient is not readily available. Because of the absence of good archival records, and the absence of reasons for changes or deviations, tracking a problem for quality control, legal or other reasons is difficult, and it is difficult to research the relative effectiveness of various interventions or to perform other research from the records.

The lack of a complete archival record can also cause significant problems for healthcare professionals who must adequately document the examination and treatment of patients whose medical bills are being paid by insurance companies. If the healthcare professional does not provide proper documentation, the insurance companies will not pay the bills. Furthermore, healthcare professionals have less time to spend with each patient these days. As a result, the healthcare professional does not have time to figure out from the original chart and the added progress notes, if they are available, the previous problems of the patient and what treatments were prescribed. Thus, the healthcare professional needs to have an easy way to review charts for each patient.

Even with computer based patient chart and/or progress note systems, many of the problems indicated above still exist. Such systems also in many instances lack flexibility so as to be configurable by the healthcare professional so as to provide specific help in determining diagnoses and for prompting the healthcare professional with lists of symptoms, questions which should be asked and tests that should be performed in certain circumstances. In addition, they frequently do not give the healthcare professional the ability to add special instructions or to add items as required. Further, it is generally not possible to obtain either an updated chart or historical chart upon request. Thus, there is a need for a computer based medical system which enhances the diagnostic, management and documentation capabilities of a healthcare provider, and provides patient charts as well as updated or historical care plans.

SUMMARY OF THE INVENTION

It is an object of the present invention to overcome the problems cited above by providing a method and apparatus for helping healthcare professionals create clinical protocols or assist in direct entry of medical findings into a chart by intelligently prompting a healthcare professional with medical findings associated with at least one medical finding which has already been entered in the protocol. First of all, at least one medical finding for a patient is inputted into the system wherein each finding is assigned a point value for each diagnosis within a knowledge base. A total number of points for each diagnosis is then totalled for all of the findings which have been entered into the system. The possible diagnoses are then ranked in descending point total and a predetermined plurality of the highest ranked diagnoses are selected. Once the highest ranked diagnoses have been selected, the healthcare professional is prompted with additional findings associated with the selected diagnoses which have not yet been inputted into the clinical protocol.

BRIEF DESCRIPTION OF THE DRAWINGS

These and other features and advantages of the present invention will be readily apparent to one of ordinary skill in the art from the following written description, used in conjunction with the drawings, in which.

DETAILED DESCRIPTION

Figure 1:
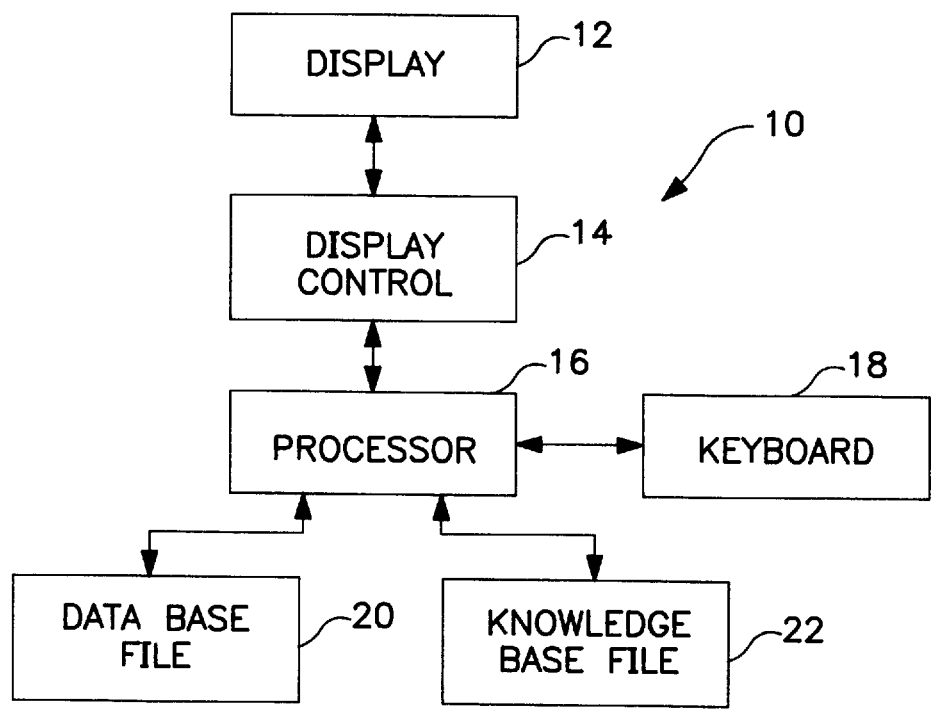
FIG. 1 illustrates a block diagram of a computer based medical system according to one embodiment of the present invention.

The present invention uses a computer based medical system to intelligently prompt a healthcare professional with lists of medical findings the healthcare professional can use when creating a clinical protocol. A block diagram of the computer based medical system suitable for use in practicing the teachings of the present invention is illustrated in FIG. 1. The medical system 10 contains a processor 16 with one or more input devices such as a keyboard 18. The processor 16 also has a database file or memory 20 and a knowledge base file or memory 22. The processor 16 operates a standard display controller 14 which in turn, controls a display device 12 at the work station. The display device 12 can be any standard type of display monitor, attached or wireless. Furthermore, the apparatus 10 can be networked to other such medical systems not illustrated which can be placed around a hospital or healthcare facility. This allows multiple people to use the medical system for the same or for multiple patients.

The present invention is based upon medical findings. Medical findings are defined as symptoms, history, physical findings, diagnoses, tests, and therapy which may be present for a particular patient. The database file 20 contains over 50,000 such medical findings and are divided into categories such as symptoms, history, physical findings, diagnoses, tests, and therapy. Furthermore, the descriptions of the medical findings stored in the database file 20 are hierarchical and can have up to eight levels of description. The first level gives the simplest explanation of a medical finding, for example, a cough. The explanations become more detailed the lower the level. As noted above, a first level finding may be a cough, while a second level finding may be a brassy cough. Another feature of the database file 20 is that all of the medical findings are uniquely named. For example, each medical finding can be assigned an internal number which uniquely identifies that particular medical finding. In addition, each medical finding also contains a code which indicates which category within the database file 20 the medical finding is associated with. For example, a medical finding may contain the code SYM to indicate that the medical finding is associated with the symptoms section; HIS to indicate that the medical finding is associated with the history section; PHY to indicate that the medical finding is associated with the physical section; DIS to indicate that the medical finding is associated with the diagnoses section; TST to indicate that the medical finding is associated with the test section; and RX to indicate that the medical finding is associated with the therapy section.

As noted above, the medical system 10 also contains a knowledge base file 22. The knowledge base file 22 contains a detailed description of over 2,000 diagnoses. The detailed description of the diagnoses uses the medical finding terms which are stored in the database file 20. For each diagnosis, each medical finding associated with the diagnosis is assigned a numerical value depending on how important such a medical finding may be to the diagnosis. For example, in the detailed description of the diagnosis for coronary artery stenosis, medical findings such as chest pain or discomfort and dyspnea (shortness of breath), which are strong showings of coronary artery stenosis, will be given high values while a lack of an appetite may not be described in the diagnoses at all or given a very low value. In one embodiment of the present invention, medical findings are assigned values between 1 and 20 wherein the value 20 is the highest value that can be given to an important medical finding, however the invention is not limited thereto. Thus, the values assigned to each medical finding within the detailed description is proportional to how important such a medical finding is to the diagnosis. Furthermore, the values can vary for a given medical finding depending on a plurality of factors such as age of the patient and timeframe, i.e., when a symptom occurred in relation to other symptoms. For example, a white blood cell count of 18,000 may be given a high value if the patient is an adult while the same medical finding is not given a value at all if the patient is a new-born child because this is normal for a new-born child.

Here again, the medical findings used in the detailed descriptions of the diagnoses are all coded, with their respective internal numbers. In addition, over 400,000 links are provided between the database file 20 and the knowledge base file 22. In other words, the findings in the database file 20 occur over 400,000 times in the knowledge base memory 22.

The detailed description of the diagnoses stored in the knowledge base file 22 contains lists of symptoms as well as personal and family history and physical findings which a patient should or may have experienced. In addition, the detailed diagnoses contain lists of tests, possible therapies, and medications which may be prescribed for the patient if the healthcare professional decides that the patient is experiencing a particular illness or problem.

Figure 2:
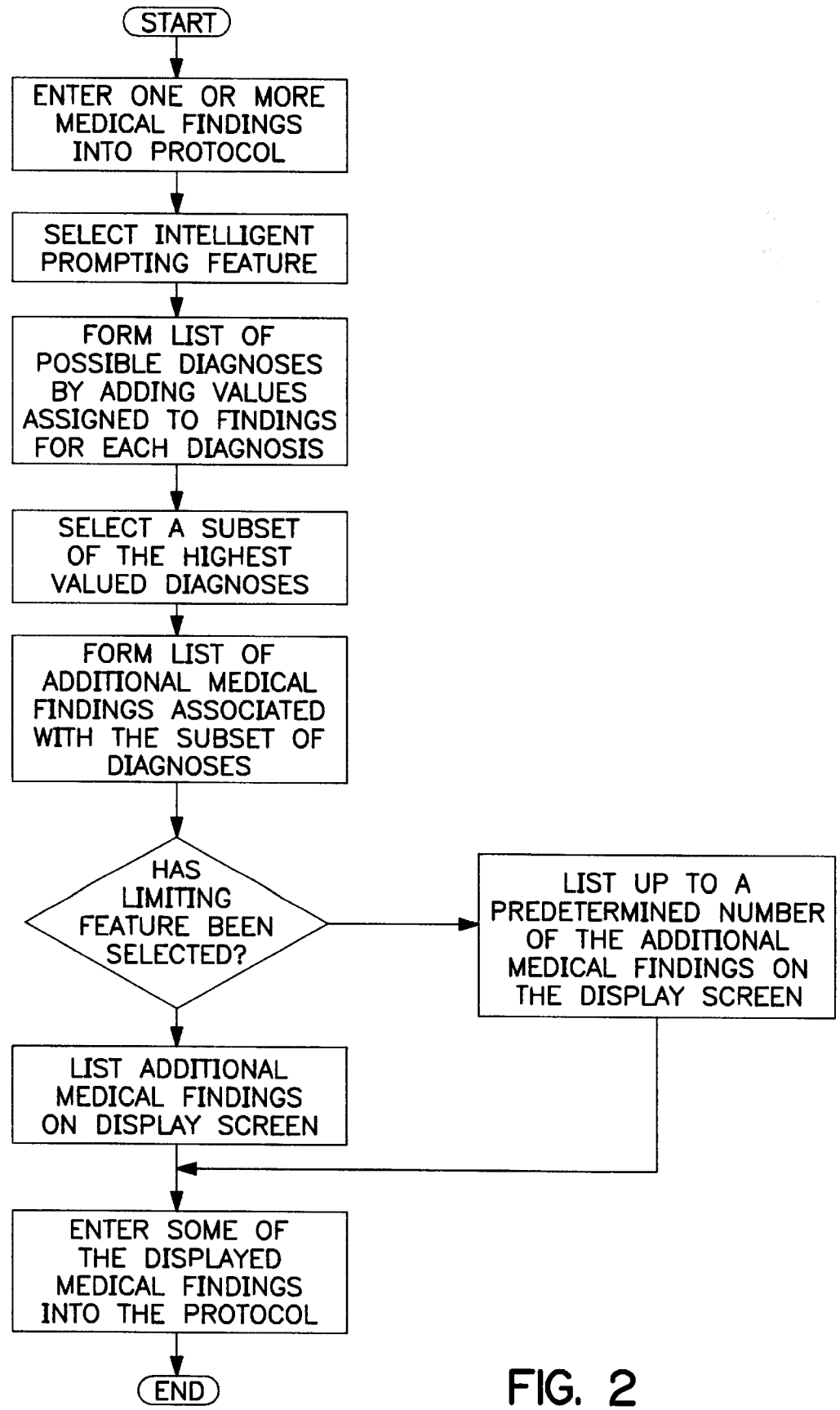
FIG. 2 illustrates a flow chart describing the operation of one embodiment of the present invention.

According to one embodiment of the present invention, it is possible for a healthcare professional to use the present invention when creating clinical protocols which can be used as a guideline for examining and treating a patient. The present invention will now be described in more detail with reference to the flow chart illustrated in FIG. 2 which describes the operation of this embodiment of the present invention. First of all, the healthcare professional may enter one or more medical findings into the computerized medical system into a clinical protocol. Clinical protocols are a structured combination of coded medical phases selected from a structured medical database of coded phases and is presented in the order of appearance desired by the healthcare professional. The healthcare professional selects at least one medical finding to start creating the clinical protocol.

Since the medical findings are coded, upon selection of the medical findings for the clinical protocol, the entered information is automatically structured in the protocol in the same format as the medical database used to build the protocols, i.e., divided into specific sections. That is, symptoms automatically go into the symptoms section, physical findings go into the physical examination section, diagnosis goes into the assessment section, etc. The creation of protocols is described in U.S. patent application Ser. No. 08/609,828, entitled "Creating and Using Protocols to Create a Patient Chart" which is being filed concurrently herewith and is expressly incorporated herein by reference. The healthcare professional then selects the intelligent prompting feature of the present invention.

When the intelligent prompting feature is selected, the computerized medical system takes each medical finding entered into the protocol and builds an internal list of possible diagnoses. The list of possible diagnoses is formed by using the point values assigned to each medical finding for each diagnosis stored in the knowledge base file 22. When all of the medical findings have been added together for each diagnosis, the diagnoses are ranked in descending point total. The computerized medical system then selects a predetermined number of diagnoses. For example, the computerized medical system could select the top five diagnoses. It will be understood that while the computerized medical system may be set to a default value, it may be possible for a healthcare professional to change the system so as to only use, for example, the top two diagnoses or the top 10 diagnoses, depending on the desires of the healthcare professional.

Once the top diagnoses have been selected, the computerized medical system will prompt the healthcare professional with other medical findings which have not been entered into the protocol but which may occur or are associated with, the top diagnoses. Thus, with a list of medical findings displayed for the healthcare professional, the healthcare professional can add new medical findings to the protocol which will remind the healthcare professional to check for certain medical findings.

Since the prompted list of medical findings may be quite large if there are numerous highly descriptive diagnoses which are selected during the intelligent prompting feature, the present invention can rank all of the findings which have not yet been entered into the protocol by the maximum range of points in each diagnosis. Then, all the findings with less than a specific number of points can be eliminated from the prompted list, thereby not encumbering the healthcare professional with a cumbersome list of possible medical findings. However, according to one embodiment of the present invention, all medical findings which are in the top two hierarchical levels in the finding database are presented with the prompted list regardless of whether their specified point totals are less than the predetermined number. Furthermore, the prompted list of medical findings may be displayed in descending point value.

For example, a healthcare professional may want to create a protocol for patients experiencing chest pains. The healthcare professional may then enter the medical findings of chest pain or discomfort and dyspnea into the computerized medical system and select the intelligent prompting feature. The medical system will add up all of the point totals for the chest pain or discomfort finding and the dyspnea finding and generate an internal list of diagnoses. In this example, the medical system will generate an internal list containing the following diagnoses: (1) coronary artery stenosis, (2) angina pectoris, (3) chronic reflux esophagitis, (4) acute myocardial infraction, and (5) pulmonary embolism. The system then generates a list of all of the medical findings associated with the diagnoses in the internal list that have not yet been entered into the protocol. The medical system will then prompt the healthcare professional with a list of additional medical findings from which the healthcare professional may select and add to the clinical protocol being created. As explained above, the list of additional medical findings can be limited so as not to encumber the healthcare professional with a cumbersome list of possible medical findings. The healthcare professional, after adding several more medical findings, may again select the intelligent prompting feature to generate a new list of diagnoses and another prompted list of medical findings.

As noted above, the medical findings are divided into six subjects or sections (symptoms, history, physical findings, diagnosis, tests, and therapy). Thus, the healthcare professional may select from which section of medical findings the healthcare professional wants to be prompted from when using the intelligent prompting feature. For example, the healthcare professional may select the section of symptoms when building the clinical protocol. Thus, the medical system will provide a list of other symptoms from the top selected diagnoses generated by the intelligent prompting feature.

According to another embodiment of the present invention, the intelligent prompting feature can also be used when creating a patient chart. For example, after the healthcare professional has entered several medical findings into a patient chart, the healthcare professional can select the intelligent prompting feature. The medical system will then generate a list of most likely diagnoses based upon the point values assigned to the entered medical findings. A list of additional medical findings will then be displayed on the display screen.

It will be appreciated by those of ordinary skill in the art that the present invention can be embodied in other specific forms without departing from the spirit or essential character thereof. The presently disclosed embodiments are therefore considered in all respects to be illustrative and not restrictive. The scope of the invention as indicated by the appended claims rather than the foregoing description, and all changes which come within the meaning and range of equivalents thereof are intended to be embraced therein.

I claim:

1. A method for intelligently prompting a user with a list of medical findings when the user is creating a medical document, comprising the steps of:
    (a) inputting at least one medical finding into the medical document, wherein each medical finding is assigned a point value for each diagnosis;
    (b) calculating a total number of points for each diagnosis after the medical findings have been entered;
    (c) selecting at least one diagnosis from those having highest point totals;
    (d) prompting the user with a list of additional medical findings which are associated with the selected diagnoses and which have not yet been inputted into the medical document so that the user can select some of the additional medical findings for addition to the medical document; and
    (e) repeating steps (b)–(d) when additional medical findings are inputted into the medical document so as to dynamically recreate the list of medical finding based on all of the inputted medical findings, wherein the point value for each medical finding for each diagnosis may change from the originally assigned point value with the passage of time.

2. A method according to claim 1, wherein only findings with point values above a predetermined level are provided to the user.

3. A method according to claim 1, further comprising the steps of:
    ranking the possible diagnoses in descending point total value; and
    selecting a predetermined plurality of highest ranked diagnoses.

4. A method according to claim 3, further comprising the step of:
    prompting a user with additional findings associated with the selected diagnoses which have not yet been inputted.

5. A method according to claim 4, wherein only medical findings with point values above a predetermined level are provided to the user.

6. A method according to claim 3, wherein the five highest ranked diagnoses are selected.

7. The method of claim 1, wherein the point value of at least one of the medical findings for at least one of the diagnoses is based on an age of the patient.

8. The method of claim 1, wherein the point value of at least one of the medical findings for at least one of the diagnoses varies with an age of the patient.

9. The method of claim 1, wherein a point value of at least one of the medical findings for at least one of the diagnoses is based on when the at least one medical finding occurred relative to others of the medical findings.

10. A device for intelligently prompting a user with a list of medical findings when the user is creating a medical protocol, comprising:

storage means for storing a list of possible diagnoses and a plurality of medical findings associated with each diagnosis, wherein each medical finding for each diagnosis has been assigned a numerical value;

means for entering medical findings into said device and adding the entered medical findings to the medical protocol;

means for calculating a point total for each diagnosis based upon the medical findings which have been entered;

means for selecting at least one diagnosis from those having highest point totals; and means for prompting a user on a display with additional findings which are associated with the selected at least one diagnosis and which have not yet been entered;

wherein after the user adds at least one of the additional medical findings to the medical protocol, the calculating means recalculates the point totals for each diagnosis based on all of the medical findings in the medical protocol, the selecting means selects at least one diagnosis from those having highest point totals, and the prompting means prompts the user with additional finding which are associated with the newly selected at least one diagnosis and which have not yet been entered.

11. A device according to claim 10, wherein only findings with numerical values above a predetermined value are provided to the user.

12. A device according to claim 10, further comprising:

means for ranking the possible diagnoses in descending point total; and means for selecting a predetermined plurality of a highest ranked diagnoses.

13. A device according to claim 12, further comprising:

means for prompting a user with additional findings associated with the selected diagnosis which have not been entered.

14. A device according to claim 13, wherein only findings with point values above a predetermined level are provided to the user.

15. A device according to claim 12, wherein the five highest ranked diagnoses are selected.

* * * * *